(12) United States Patent
Will et al.

(10) Patent No.: US 11,302,423 B2
(45) Date of Patent: Apr. 12, 2022

(54) PREDICTING PATIENTS WHO CAN BENEFIT FROM A CLINICAL TRIAL

(71) Applicant: International Business Machines Corporation, Armonk, NY (US)

(72) Inventors: Eric W Will, Rochester, MN (US); Adam Clark, Mantorville, MN (US)

(73) Assignee: International Business Machines Corporation, Armonk, NY (US)

( * ) Notice: Subject to any disclaimer, the term of this patent is extended or adjusted under 35 U.S.C. 154(b) by 212 days.

(21) Appl. No.: 16/254,770

(22) Filed: Jan. 23, 2019

(65) Prior Publication Data

US 2020/0234800 A1 Jul. 23, 2020

(51) Int. Cl.
G16H 10/20 (2018.01)
G16H 50/20 (2018.01)
G16H 10/60 (2018.01)

(52) U.S. Cl.
CPC ............ G16H 10/20 (2018.01); G16H 10/60 (2018.01); G16H 50/20 (2018.01)

(58) Field of Classification Search
CPC .......... G16H 10/00; G16H 80/00; G06F 1/00; G06F 2221/00; G06Q 10/00; G06Q 2250/00
See application file for complete search history.

(56) References Cited

U.S. PATENT DOCUMENTS

| | | | |
|---|---|---|---|
| 2012/0041779 A1* | 2/2012 | Boroczky | G16H 40/63 705/2 |
| 2014/0122113 A1 | 5/2014 | Hoffman, Jr. et al. | |
| 2016/0246932 A1* | 8/2016 | Allen | G16H 20/40 |
| 2017/0098385 A1* | 4/2017 | Martucci | G16H 30/40 |

(Continued)

FOREIGN PATENT DOCUMENTS

| | | | | |
|---|---|---|---|---|
| EP | 2145276 A1 * | 1/2010 | | G16H 50/20 |
| WO | 2016203457 A1 | 12/2016 | | |

OTHER PUBLICATIONS

Majeed RW, Röhrig R. "Identifying patients for clinical trials using fuzzy ternary logic expressions on HL7 messages", Stud Health Technol Inform. 2011;169:170-4 (Year: 2011).*

(Continued)

*Primary Examiner* — Devin C Hein
(74) *Attorney, Agent, or Firm* — Patterson + Sheridan, LLP (57) ABSTRACT

Method and apparatus for predicting beneficial clinical trials for patients. Embodiments include receiving one or more attributes of a first patient. Embodiments include selecting a potential clinical trial for the first patient, based on the one or more attributes. Embodiments include identifying a cohort of patients that are clinically similar to the first patient, based on the one or more attributes, wherein each patient in the cohort has undergone a respective trial that is either (i) the potential clinical trial, or (ii) a clinically similar clinical trial. Embodiments include determining, for each respective patient in the cohort, a respective outcome of the respective trial. Embodiments include generating a predicted outcome for the first patient, based on the respective outcomes for each patient in the cohort. Embodiments include refraining from recommending the potential clinical trial for the first patient, based on the predicted outcome.

20 Claims, 5 Drawing Sheets

(56) References Cited

U.S. PATENT DOCUMENTS

2018/0046780 A1    2/2018  Graiver et al.
2018/0315505 A1*  11/2018  Itu .......................... G16H 50/20
2020/0168305 A1*   5/2020  Bashir .................... G06N 20/00

OTHER PUBLICATIONS

Zhe He et al.; A Method for Analyzing Commonalities in Clinical Trial Target Populations; https://www.ncbi.nlm.nih.gov/pmc/; Nov. 14, 2014; NCBI.

* cited by examiner

PREDICTING PATIENTS WHO CAN BENEFIT FROM A CLINICAL TRIAL

BACKGROUND

The present disclosure relates to using machine learning techniques to deliver clinical trial recommendations, and more specifically, to predicting beneficial clinical trials for patients.

Clinical trials in medicine are research studies that are used to test and evaluate various medical treatments, drugs, or devices under development. Typically, clinical trials are defined as a treatment, drug, or device being developed, qualifying criteria (or inclusion criteria) defining the characteristics of patients who may be eligible to participate in a specified trial, and disqualifying criteria defining the characteristics of patients who are not eligible for participation in the trial. For example, the qualifying criteria may include the medical condition that the subject of the clinical trial is addressing, a stage of medical treatment that patients should be at, what previous treatments a patient may have received prior to entering the clinical trial, and the like. The disqualifying criteria defining the characteristics of patients who are not eligible to participate in a specified trial may include, for example, a stage of a disease beyond which a patient would be ineligible for inclusion in the trial, previous treatments that disqualify a patient from participating in the trial, and the like. However, qualifying and disqualifying criteria and other relevant information about clinical trials may sometimes be written in a non-standardized format that cannot easily be cross-compared.

At any given time, a patient may potentially be eligible for participation in a variety of clinical trials. Typically, to determine what clinical trial(s) a patient may be eligible for participation in, the patient's doctors and/or other clinical staff may review the patient's medical records and the qualifying and disqualifying criteria for a number of clinical trials to identify trials that may be of interest to the patient. However, the process of identifying trials that are potentially of interest for the patient may be a time consuming, manual process that requires doctors or other clinical staff to compare potentially voluminous patient records with at least the qualifying and disqualifying criteria for each clinical trial. Further, due to the number and wide variety of clinical trials that may be active at any time, manual searches for trials of interest may miss potentially relevant trials for a given patient. In some cases, manual analysis of potential clinical trials to enroll a patient in may rely on institutional procedures that prioritize clinical trials being run in certain institutions over potentially relevant clinical trials run in other institutions, which may result in potentially relevant clinical trials for a patient being overlooked or otherwise omitted from consideration.

Automated methods for analyzing patient records and clinical trial definitions may not be able to accurately match patients with the clinical trials that patients may be eligible to participate in for various reasons. For example, automated methods may not be able to accurately parse the intent of statements in a clinical trial definition. In another example, automated methods may not be able to understand the implications of a patient's medical records with respect to the ability to successfully complete or receive benefit from a clinical trial. In still further examples, automated methods may be unable to determine or identify temporal relationships associated with qualifying or disqualifying criteria for a clinical trial. As such, there is a need in the art for improved techniques for automatically recommending clinical trials for patients.

SUMMARY

According to one embodiment of the present invention, a method includes receiving one or more attributes of a first patient; selecting a potential clinical trial for the first patient, based on the one or more attributes; identifying a cohort of patients that are clinically similar to the first patient, based on the one or more attributes, wherein each patient in the cohort has undergone a respective trial that is either (i) the potential clinical trial, or (ii) a clinically similar clinical trial; determining, for each respective patient in the cohort, a respective outcome of the respective trial; generating a predicted outcome for the first patient, based on the respective outcomes for each patient in the cohort; and refraining from recommending the potential clinical trial for the first patient, based on the predicted outcome. In certain embodiments, a computing system may be configured to perform methods described herein. In some embodiments, a computer-readable storage medium may store instructions that, when executed by one or more processors, cause the one or more processors to perform methods described herein.

DETAILED DESCRIPTION

Embodiments presented herein involve techniques for predicting beneficial clinical trials for patients. One or more machine learning models may be trained using historical clinical trial data and historical patient data of a plurality of patients in order to predict outcomes for clinical trials based on attributes of a given patient.

In one example, attributes of historical patients that participated in historical clinical trials are used along with information related to the outcomes of the historical clinical trials to train the model(s) to associate certain particular attributes with particular outcomes for clinical trials. The trained model(s) are then used to predict outcomes for clinical trials based on attributes of a given patient. Predicted outcomes may, for example, take the form of scores indicating a degree of benefit (e.g., a score of 0 may indicate that the clinical trial will provide no benefit for the patient while a score of 100 may indicate that the clinical trial will be of maximum benefit, such as resulting in a complete cure). As such, techniques described herein allow for accurate and dynamic automated prediction of clinical trials that are likely to be of benefit to a given patient based on the patient's attributes in view of historical attributes of patients that have participated in clinical trials.

Figure 1:
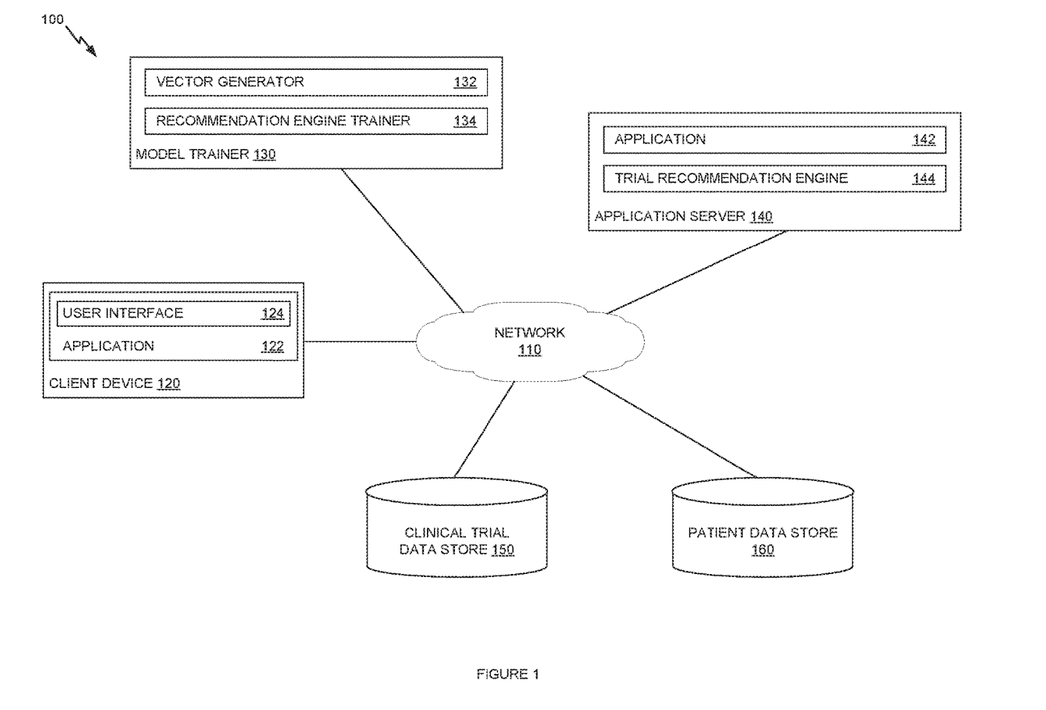
FIG. 1 illustrates an example networked environment in which predictive models are used to predict beneficial clinical trials for patients, according to one embodiment.

FIG. 1 illustrates an example networked computing environment in which predictive models are used to predict beneficial clinical trials for patients. As illustrated, computing environment 100 includes a client device 120, a model trainer 130, an application server 140, a clinical trial data store 150, and a patient data store 160, connected via network 110.

Client device 120 generally is representative of a computing device on which a user can define and/or manage the training of predictive models used by trial recommendation engine 144 to recommend potentially relevant clinical trials for a patient and access application 142 on application server 140 to obtain a set of potentially relevant clinical trials for a patient. Client device 120 may be, for example, a laptop computer, a desktop computer, a thin client, a tablet computer, a mobile computing device, and the like.

Client device 120 includes an application 122 (e.g., a client side component of a client-server application) comprising a user interface 124, which allows a user of client device 120 to interact with a server side component, such as application 142 on application server 140. User interface 122 may, for instance, allow a user of client device 120 to initiate a search for recommended clinical trials that may be of interest to a patient by providing, to application server 140, identifying information of the patient (e.g., the patient name, date of birth, social security number, and/or the like) and/or the patient's medical records (e.g., entered in a standardized format or scanned copies of records that can be processed to determine patient attributes) in a request for one or more potentially relevant clinical trials to present to a patient.

Model trainer 130 generally uses information about patients that previously participated in in trials (e.g., from patient data store 160) along with the criteria defined for those trials and information about the outcomes of those trials (e.g., from clinical trial data store 150) to train one or more predictive models used in predicting outcomes of clinical trials for patients based on patient attributes. As illustrated, model trainer 130 includes a vector generator 132 and a recommendation engine trainer 134. The training data may include a first set of labeled data used to train the predictive models and a second set of unlabeled data (e.g., for which the intended label is known) used to verify the accuracy of the trained predictive models and to refine the trained predictive models prior to deployment to application server 140.

Vector generator 132 generates a training data set for use by recommendation engine trainer 134 to train a predictive model for predicting outcomes of clinical trials for a patient based on patient medical history (e.g., in the form of patient attributes). To generate the training data set, vector generator 132 can obtain information about previously completed clinical trials from clinical trial data store 150 and patient medical history data from patient data store 160. The information obtained from clinical trial data store 150 may include, for example, a roster of patients enrolled in a specific clinical trial and a definition of that clinical trial. The definition of the clinical trial may include qualifying and disqualifying criteria, patient requirements for participation in the trial, a trial enrollment deadline, and other information defining the clinical trial. The roster of patients may include information identifying each patient that vector generator 132 can use to obtain patient medical records from patient data store 160, information identifying whether each patient successfully completed the trial, and information related to the outcomes of trials for patients (e.g., whether or not a patient's condition improved following the trial and/or other data related to the effects of clinical trials on patients, such as patients' feedback about trials). In certain embodiments, information retrieved from clinical trial data store 150 includes data regarding whether a condition of a patient improved, worsened, or remained unchanged, a length of time before an outcome was observed, and/or a set of side effects experienced by a patient as a result of a given clinical trial.

A training data set may include, for example, a plurality of training data instances that include attributes of patients that participated in particular clinical trials and indicators of positive and/or negative outcomes of particular clinical trials. In some implementations, a training data instance may be in the form of a vector comprising a set of features (e.g., patient attributes such as age, gender, geographic location, medical history, and the like, along with an identifier of a clinical trial) associated with one or more labels (e.g., and an indicator of whether the clinical trial had a positive or negative outcome for the patient, which may be determined from the clinical trial data, such as based on whether positive outcome factors outweigh negative outcome factors, based on whether the data indicates that the patient's condition was objectively improved by the clinical trial, and/or based on whether the patient indicated in feedback that the trial was beneficial). It is noted that benefit can be a subjective concept, and that patient's individual preferences may affect whether a clinical trial is considered beneficial for them. As such, patient feedback about clinical trials may be the best indicator of benefit for a given patient. Furthermore, patient attributes may include patient preferences (e.g., whether a patient prefers more aggressive treatment or whether the patient is risk averse), and these preferences may be included as features in the training data to further refine benefit prediction.

To generate the training data to be used by recommendation engine trainer 134, vector generator 132 can generate a first set of training data comprising feature data and label data used to train a predictive model and a second set of labeled feature data (e.g., provided as unlabeled data to the predictive model for testing purposes) that can be used to test the generated predictive model. For example, in an embodiment where machine learning models are used to predict outcomes of clinical trials for a patient, the first set of data may comprise a plurality of vectors, where the features in each vector include information from patient medical records and identifying information of a given clinical trial, and the labels in each vector include information about the outcome of the given clinical trial (e.g., an indicator of whether the given clinical trial had a positive outcome or a negative outcome for the patient). The second set of data may comprise an unlabeled set of patient medical records of patients who have been accepted into a clinical trial, for which the outcome of the clinical trial is known but excluded from the data set for testing purposes.

In some embodiments, the first set of data may further include additional features that may be used to further refine predictions of trials that may be beneficial to a patient. These additional features may include, for example, information about a current stage of treatment that a patient is in (e.g., where the patient is at in a care pathway), the specialty of the patient's clinicians, the institution that is treating the patient, and patient completion success for other trials that the patient may have participated in. These additional features may be used to further refine the recommendations delivered by trial recommendation engine 144 to deliver more relevant recommendations to the patient's doctors. For example, in some cases (e.g., for patients with certain attributes), a clinical trial may only be beneficial after a patient has undergone a certain number of treatments. Therefore, including features in the training data indicating what stage of treatment historical patients were at when participating in clinical trials that were beneficial or not beneficial may allow for improved predictions.

For example, the use of information about a stage of treatment that the patient is in may be used to prioritize recommendations of trials relevant to that particular stage of treatment over trials relevant to earlier or later stages of treatment (e.g., where a patient is in an early stage of a disease, prioritizing clinical trials directed to curative treatments over palliative treatments that are more appropriate for patients with later or terminal stages of the disease). For example, a predictive model may be trained, using the features, to output higher scores when features of a given patient match these features associated with a beneficial clinical trial in the training data. Likewise, using information about the patient's clinicians may further indicate, at least implicitly, relevant information about the patient's conditions, such as disease progression, that may be used to prioritize some clinical trials over others (e.g., by assigning higher scores to certain clinical trials). This information may, for example, prioritize clinical trials being held at particular institutions (e.g., based on a distance metric from the patient's clinicians) based on assumptions that patients are more likely to successfully participate in trials that are more easily accessible to the patient. Finally, information about the patient's previous trial completion success may be used as an input to prioritize trials, for example, with similar or less stringent completion requirements to trials that the patient has previously successfully participated in. It should be noted, however, that these additional data points for refining the recommendation of relevant trials are not exhaustive, and other appropriate data points may be used to train predictive models for predicting beneficial clinical trials for a given patient.

Recommendation engine trainer 134 obtains the training data generated by vector generator 132 and, using supervised learning techniques, trains one or more predictive models for predicting outcomes of clinical trials for patients. Training predictive models may involve using a training data set that includes training inputs that are associated with particular training outputs (e.g., labels). As such, training data comprising historical patient attributes and identifying information of clinical trials associated with labels indicating whether or not clinical trials were beneficial is used to train one or more predictive models to predict outcome of clinical trials for patients. For example, a trained predictive model may accept a set of patient attributes and identifying information of a given clinical trial as inputs and output a score for the given clinical trial indicating how beneficial the given clinical trial is predicted to be for the patient. In other embodiments, the trained predictive model accepts patient attributes and identifying information of a plurality of clinical trials as inputs and outputs scores for each of the plurality of clinical trials (e.g., in the form of value pairs comprising identifying information of clinical trials and scores).

Predictive models described herein may be, for example, random forest models, and training a prediction model may involve building a "forest" of "trees" representing the training data, where input features are randomly permuted at each split (e.g., each division of the training data). In such embodiments, a prediction model is "trained" by constructing a plurality of decision trees based on sub-divisions of the training data that include random permutations of input features associated with labels.

It is noted that random forest techniques are only included as one example, and that other techniques may be employed for training prediction models. Other types of machine learning models, such as a Naïve Bayes model, logistic regression, decision tree, gradient-boosted tree, multilayer perceptron, and others may also be used as prediction models.

In certain embodiments a single prediction model is used, while in other embodiments a plurality (or ensemble) of prediction models may be used (e.g., for different institutions and/or for different stages of an overall process for recommending clinical trials). In some embodiments, additional attributes may be used to customize a generated prediction model and thus customize the results delivered by the trial recommendation engine 144.

For example, recommendation engine trainer 134 may generate an institutional baseline model using the training data generated by vector generator 132 reflecting institutional preferences for identifying beneficial clinical trials for a patient. Individual clinician preferences may then be used to customize the institutional default model to reflect that clinician's preferences in identifying beneficial clinical trials (e.g., based on the clinician's previous experiences with clinical trial organizers, interventions that are likely or unlikely to succeed based on prior experience, and the like).

In certain embodiments, predictive models may be trained for predicting future patient attributes based on current patient attributes, and the predicted future patient attributes may be included with current patient attributes as inputs to predictive models for predicting outcomes of clinical trials.

For instance, a patient may not currently meet a criterion for a clinical trial but a predictive model may be able to predict that the patient will meet the criterion prior to the start of the clinical trial based on historical patient attributes (e.g., other patients with patient data similar to the patient's current patient data went on to meet the criterion within a certain time frame). In one example, a clinical trial requires a patient to have undergone a certain procedure. Historical patient data may indicate that patients with certain attributes (e.g., a medical condition for a certain amount of time) typically undergo the procedure within a particular time frame. This historical patient data may be used to train a predictive model to predict whether a patient will undergo the procedure within a certain time frame based on current attributes of the patient. The output of this predictive model for a given patient may be provided along with other current attributes of the given patient as inputs to a predictive model for recommending clinical trials for the patient. For example, if the value of an attribute is predicted to change prior to the start of the clinical trial, the predicted future value of this attribute may be provided as an input to the predictive model rather than the current value of the attribute. As such, techniques described herein allow for recommending clinical trials not only based on the patient's current attributes, but also based on attributes that the patient is predicted to have in the future.

Application server 140 includes an application 142 and a trial recommendation engine 144. Application 142 may be any type of application in which users can request recommendations of potentially beneficial clinical trials for a patient by providing patient data (e.g., identifying information of a patient and/or medical condition information, treatment history, prior clinical trial participation history, and other relevant information) and, in some embodiments, user-defined filters in a search request executed by application 142. Client device 120 may instantiate or initiate a session of application 142 in response to a request for application content (e.g., a list of active clinical trials that are enrolling patients for participation) generated by a user of client device 120. In some embodiments, the instance of a session of application 142 may be instantiated by a user of client device 120 accessing a home page of an application 142 structured as a web application. In other embodiments, user interface 122 may instantiate the instance of application 142 by launching an executable file on client device that includes components that execute locally on client device 120 and use data provided by application 142.

During execution of application 142, a user of client device 120 may request a set of recommended clinical trials for a given patient by providing data related to that patient to application 142 in conjunction with a search request. In response, application 142 provides the received data to trial recommendation engine 144 for analysis. In some embodiments, the user may provide identifying information for a patient (e.g., name, date of birth, social security number, and/or other identifying information), and data for the patient may be retrieved (e.g., by trial recommendation engine 144) from patient data store 160 based on the identifying information. Application 142 may receive a list of potentially beneficial clinical trials for the patient (e.g., ranked in an order of predicted benefit based on scores output by predictive models described herein) from trial recommendation engine 144, as discussed in further detail below, and display the list of potentially beneficial clinical trials in user interface 122 of client device 120. In some embodiments, the list of potentially beneficial clinical trials may include a predetermined number of potentially beneficial clinical trials for the patient and may be sorted based on the rankings or scores associated with each clinical trial in the list of potentially beneficial clinical trials. Application 142 may additionally allow a user of client device 120 to further refine the list of potentially beneficial clinical trials using one or more user-defined filters. In some embodiments, application 142 also allows a user of client device 120 to "toggle" the prediction of beneficial clinical trials on and off, such that the user can alternatively receive only predictions of clinical trials for which a patient is eligible or which are predicted to be relevant to the patient rather than clinical trials predicted to be beneficial.

Trial recommendation engine 144 uses the prediction model(s) generated by recommendation engine trainer 134, as discussed above, to examine patient data for a given patient and recommend potentially beneficial clinical trials for the patient based, at least in part, on the patient's medical history. In some embodiments, trial recommendation engine 144 retrieves patient data, such as medical history, for a given patient from patient data store 160 based on identifying information of the patient (e.g., received from a user of client device 120). Patient data may include a plurality of different types of patient attributes, such as aspects of the given patient's medical history. Patient attributes may, in some embodiments, include scheduled events that have not yet occurred (e.g., medical procedures scheduled for future dates).

In some embodiments, trial recommendation engine 144 first determines a plurality of clinical trials for which the given patient is eligible based on qualifying criteria and disqualifying criteria for clinical trials (e.g., retrieved from clinical trial data store 150), such as evaluating the qualifying criteria and disqualifying criteria based on the patient attributes. In certain embodiments, trial recommendation engine 144 predicts future attributes of the given patient, such as by providing certain current attributes of the patient (e.g., retrieved from patient data store 160) as inputs to one or more predictive models that output predicted future attributes.

Trial recommendation engine 144 provides patient attributes, which may include current and predicted future attributes, of the given patient as inputs to one or more predictive models for predicting outcomes of clinical trials for the given patient. In some embodiments, trial recommendation engine 144 also provides identifying information of the clinical trials for which the given patient is eligible as inputs so that the predictive model(s) only predict outcomes for those particular clinical trials. For example, in one embodiment a predictive model accepts patient attributes as inputs and outputs a score for every clinical trial for which the predictive model was trained, while in another embodiment a predictive model accepts both patient attributes and identifiers of clinical trials as inputs and outputs scores only for the clinical trials identified in the inputs.

For example, a predictive model may process the inputs and output a predicted outcome (e.g., which may take the form of a score) for each of a plurality of clinical trials (e.g., identified by trial recommendation engine 144), each score indicating a predicted strength of benefit of a respective clinical trial to the given patient. In certain embodiments, predictive models may be trained based on individual clinician preferences for a clinician that requested the recommended clinical trials, and outputs of the predictive models may be in accord with the clinician preferences (e.g., clinical trials of a type preferred by the clinician may be assigned higher scores according to the training of the model). Techniques described herein may involve fuzzy logic, as output scores are not only based on bright-line rules (e.g., whether or not a patient meets a criterion for a clinical trial), but are based on degrees of association (e.g., the patient may not meet a certain criterion or attribute that is historically associated with a beneficial clinical trial explicitly, but may be within a threshold distance and/or may be predicted to meet the criterion or attribute prior to the time of the clinical trial). Predictive models, therefore, are a means of implementing fuzzy logic. Fuzzy logic may also be employed in determining which clinical trials a patient is eligible for (e.g., as a first step before providing patient attributes and identifying information of the clinical trials for which the patient is eligible as inputs to a predictive model).

In some embodiments, trial recommendation engine 144 may rank the plurality of clinical trials based on the scores output by the predictive model(s). Trial recommendation engine 144 may further filter the clinical trials, such as based on user input (e.g., filters and/or preferences provided by the user via user interface 122). In some embodiments, trial recommendation engine 144 also applies certain bright-line rules in order to filter the clinical trials, such as to prevent recommending a clinical trial with a low score to a user when the clinical trial would in fact not be appropriate for the user at all. For example, if a clinical trial is only for HER-2 negative patients and the given patient is HER-2 positive, then the clinical trial may be filtered out of the list of clinical trials provided to the user.

Trial recommendation engine 144 provides recommended clinical trials to application 142, which may provide the recommended clinical trials to user interface 122 for display to the user. In certain embodiments, trial recommendation engine 144 provides information to application 142 regarding attributes that were predicted so that this information can be provided to the user. For example, if trial recommendation engine 144 recommends a certain clinical trial as beneficial based on a prediction that the given patient will undergo a certain procedure in the future, then the user may be informed that the clinical trial is only recommended if the prediction turns out to be accurate.

Clinical trial data store 150 may be a data storage entity, such as a database or repository, that stores data about clinical trials. For example, clinical trial data store 150 may store qualifying and disqualifying criteria for clinical trials, rosters of patients that participated in clinical trials, information about outcomes of clinical trials, patient feedback about clinical trials, and the like. For example, the data in clinical trial data store 150 may have been entered by one or more users (e.g., clinicians, patients, or professionals), or may have been mined from various sources, such as articles and reports related to clinical trials.

Patient data store 160 may be a data storage entity, such as a database or repository, that stores data about patients. For example, patient data store 160 may store personal data, patient attributes, medical records, patient preferences, and other data related to patients, which may have been provided by one or more users, such as patients and/or clinicians.

While model trainer 130, application server 140, clinical trial data store 150, and patient data store 160 are illustrated as separate components in FIG. 1, it should be recognized that model trainer 130, application server 140, clinical trial data store 150, and patient data store 160 may be implemented on any number of computing systems, either as one or more standalone systems or in a distributed environment.

Figure 2:
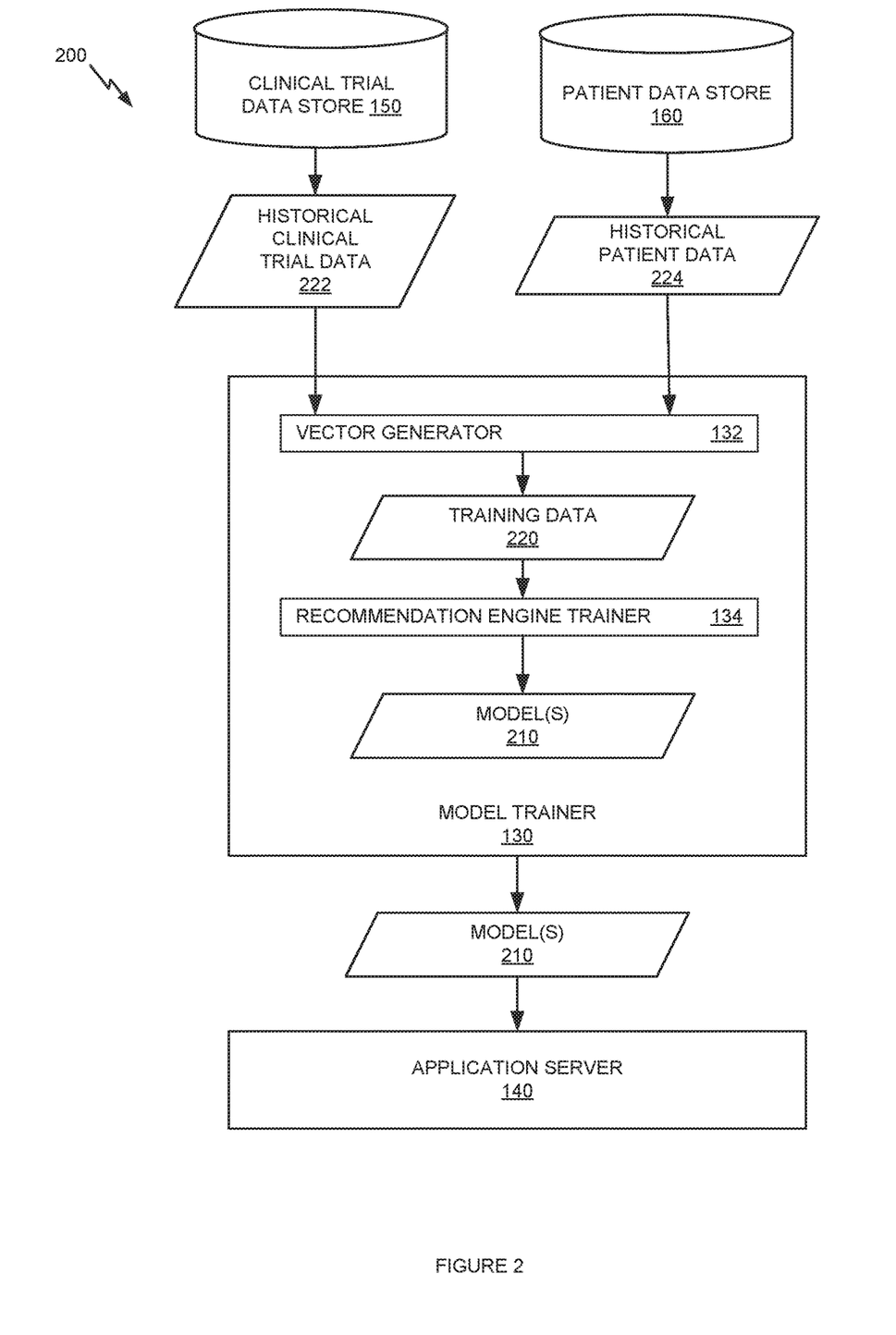
FIG. 2 illustrates an example of training predictive models for predicting beneficial clinical trials for patients.

FIG. 2 illustrates an example 200 of training predictive models for predicting beneficial clinical trials for patients. Example 200 includes model trainer 130 (comprising vector generator 132 and recommendation engine trainer 134), clinical trial data store 150, patient data store 160, and application server 140 of FIG. 1.

Model trainer 130 retrieves historical clinical trial data 222 from clinical trial data store 150 and historical patient data 224 from patient data store 160. Historical clinical trial data 222 may include information regarding qualifying and disqualifying criteria for a plurality of clinical trials. Historical clinical trial data 222 may also include lists of patients (e.g., identified using information such as names, dates of birth, and social security numbers) that participated in historical clinical trials and information relating to the outcomes of the clinical trials, such as whether or not a given patient found a clinical trial to be beneficial or whether the patient's condition improved as a result of the clinical trial.

Historical patient data 224 may include attributes of patients that participated in historical clinical trials (e.g., retrieved based on identifying information of the patients included in historical clinical trial data 222), such as medical history of the patients and preferences of the patients.

Vector generator 132 uses historical clinical trial data 222 and historical patient data 224 to generate training data 220 for generating one or more trained models 210. For example, training data 220 may include a plurality of training data instances (e.g., vectors) associating historical patient attributes with indicators of whether or not certain clinical trials were beneficial. Training data 220 is provided to recommendation engine trainer 134, which uses training data 220 to generate one or more trained models 210, such as using various supervised machine learning concepts. One or more of models 210 may be trained to predict outcomes of clinical trials (e.g., scores indicating a strength of benefit) in response to input patient attributes and identifying information of the clinical trials. In some embodiments, one or more of models 210 are trained based on specific clinician preferences and are used to recommend beneficial clinical trials for patients when requested by certain clinicians. For example, training data 220 may further include data related to clinician preferences, and the clinician preferences may be used to adjust the weights of features within the models.

Model trainer 130 provides the one or more models 210 to application server 140, which loads the one or more models 210 into memory for use in recommending beneficial clinical trials for patients.

Figure 3:
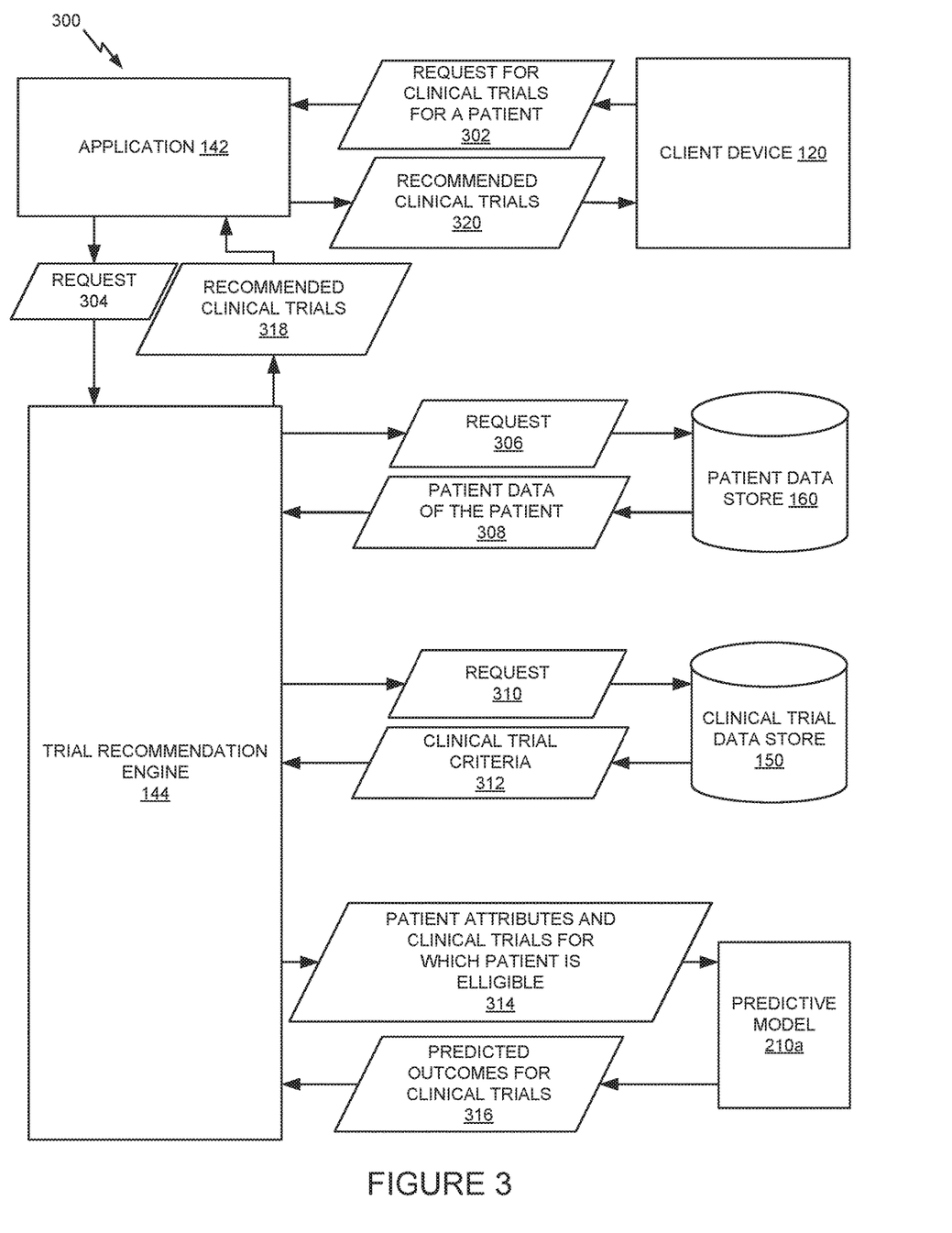
FIG. 3 illustrates an example of using trained predictive models to predict beneficial clinical trials for patients.

FIG. 3 illustrates an example 300 of using trained predictive models to recommend beneficial clinical trials to patients. Example 300 includes client device 120, application 142, trial recommendation engine 144, patient data store 160, and clinical trial data store 150 of FIG. 1. Example 300 also includes predictive model 210a, which may be one of model(s) 210, trained as illustrated in example 200 of FIG. 2. In example 300, predictive model 210a is trained to predict outcomes of clinical trials for patients based on patient attributes and identifying information of the clinical trials.

Client device 120 sends a request 302 for clinical trials for a patient to application 142. For example, a user may have initiated a request for clinical trials for the patient via a user interface of client device 120. Request 302 may include identifying information of the patient. Application 142 sends a request 304 to trial recommendation engine 144 based on request 302, such as including the identifying information of the patient.

Trial recommendation engine 144 sends a request 306 to patient data store 160 for patient data related to the patient identified in requests 302 and 304. Patient data store 160 provides patient data 308 of the patient to trial recommendation engine 144 in response to request 306. Patient data 308 may, for instance, include patient attributes such as aspects of the patient's medical history (e.g., diagnoses, procedures, allergies, medications, family medical history, and the like) and patient preferences.

Trial recommendation engine 144 then sends a request 310 to clinical trial data store for clinical trial criteria 312, which may comprise qualifying and disqualifying criteria of a plurality of clinical trials (e.g., all clinical trials for which criteria are store in clinical trial data store 150). Trial recommendation engine 144 determines which clinical trials the patient may be eligible for by determining whether the patient satisfies the qualifying criteria and/or disqualifying criteria (e.g., exactly or within a certain threshold distance using fuzzy logic) based on patient data 308. As such, trial recommendation engine 144 determines the set of clinical trials for which the patient is eligible.

Trial recommendation engine 144 then provides inputs 314 to predictive model 210a, including patient attributes determined from patient data 308 and identifying information of the clinical trials for which the patient is eligible. Predictive model 210a provides predicted outcomes 316 for the clinical trials to trial recommendation engine 144. The predicted outcomes 316 may, for example, be output in the form of a set of value pairs, each pair including an identifier of a clinical trial and a score indicating a strength of benefit of the clinical trial with respect to the patient.

Trial recommendation engine 144 receives the predicted outcomes 316 output by predictive model 210a and, in some embodiments, ranks the clinical trials based on the predicted outcomes 316 (e.g., by score). Trial recommendation engine 144 may also apply one or more filters and/or rules to the clinical trials in order to further refine the list. Trial recommendation engine 144 then provides the recommended clinical trials 318 to application 142 in response to request 304. Application 142 provides the recommended clinical trials 320 received at 318 to client device 120 for display to the user in response to request 302. For example, client device 120 may display a ranked list of recommended clinical trials 320 via a user interface that lists clinical trials likely to be beneficial to the patient. For example, the user may have toggled a user interface option indicating that the user would like to view clinical trials predicted to be beneficial to the patient.

While example 300 depicts recommending beneficial clinical trials for a single patient, it is noted that techniques described herein may also be used to recommend beneficial clinical trials for a plurality of patients, such as in response to a request from a clinician.

Figure 4:
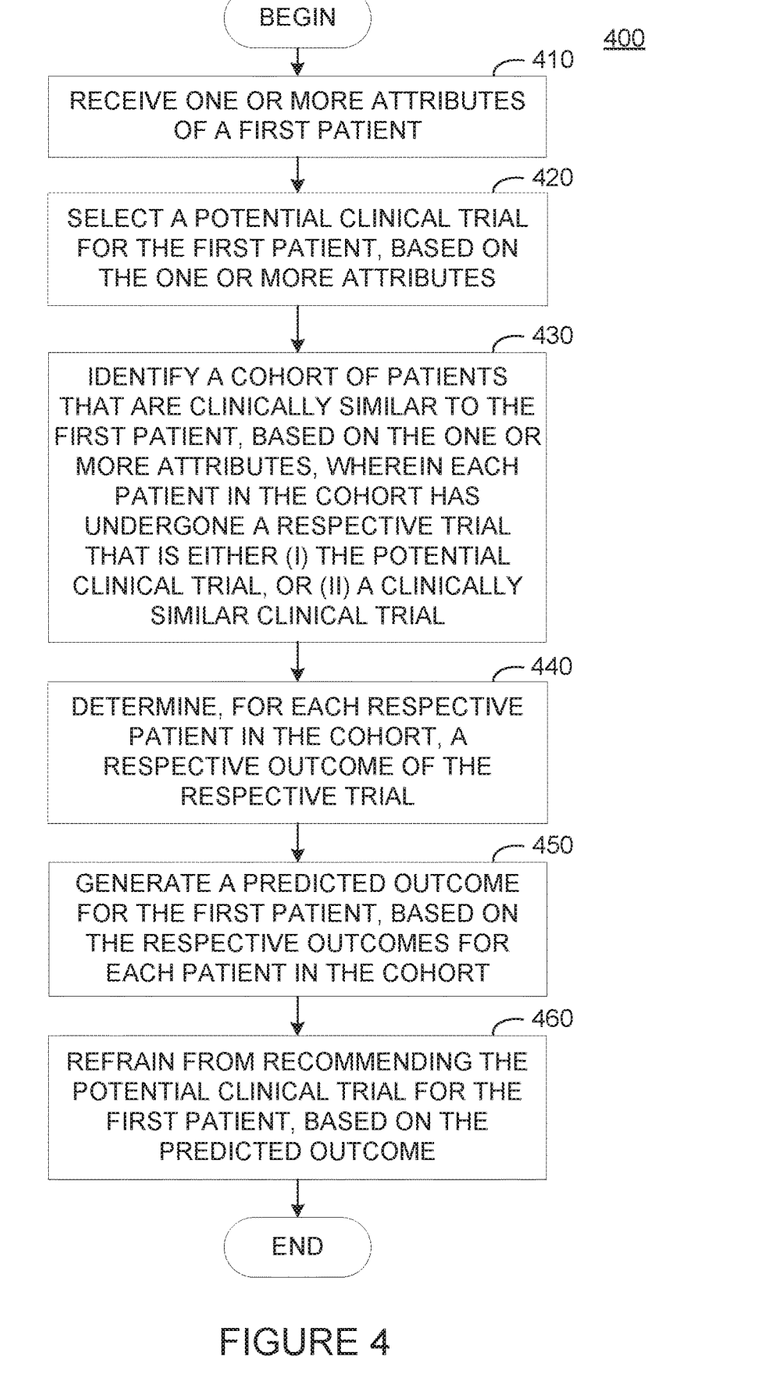
FIG. 4 illustrates example operations for predicting beneficial clinical trials for patients.

FIG. 4 illustrates example operations 400 for predicting beneficial clinical trials for patients. For example, operations 400 may be performed by trial recommendation engine 144 of FIGS. 1 and 3.

At step 410, one or more attributes of a first patient are received. For example, a user of a client device may have requested a list of clinical trial relevant to the first patient, and the first patient may have been identified in the request, such as by identifying information of the first patient. Trial recommendation engine 144 of FIG. 1 may receive the request and retrieve the one or more attributes of the first patient (e.g., from patient data store 160 of FIG. 1) based on the request. The one or more attributes may, for example, include aspects of the first patient's medical history, preferences of the first patient, and the like.

At step 420, a potential clinical trial is selected for the first patient based on the one or more attributes. For example, trial recommendation engine 144 of FIG. 1 may retrieve qualifying and disqualifying information for a plurality of clinical trials (e.g., from clinical trial data store 150 of FIG. 1) and evaluate the qualifying and disqualifying criteria based on the one or more attributes of the first patient to identify clinical trials for which the first user is eligible. The potential clinical trial may, for instance, be a clinical trial for which the first patient is determined to be eligible.

At step 430, a cohort of patients that are clinically similar to the first patient are identified based on the one or more attributes, wherein each patient in the cohort has undergone a respective trial that is either (i) the potential clinical trial, or (ii) a clinically similar clinical trial. For example, trial recommendation engine 144 of FIG. 1 may provide the one or more attributes and an identifier of the potential clinical trial as inputs to a predictive model, which may be used to identify the cohort, which may comprise patients that share similar attributes with the first patient and who have undergone either the potential clinical trial or a clinical trial that shares common characteristics, such as qualifying and disqualifying criteria, with the potential clinical trial. Clinically similar patients may be patients that share common attributes (e.g., medical history and/or preferences) and clinically similar clinical trials may be clinical trials that share common characteristics, such as clinical trials that tested a same or similar treatment option.

At step 440, for each respective patient in the cohort, a respective outcome of the respective trial is determined. For example, the predictive model may be used to identify whether the potential clinical trial or clinically similar clinical trial was beneficial for each respective patient in the cohort. It is noted that in some embodiments the predictive model stores a binary indicator of whether or not a clinical trial was beneficial for a given patient, while in other embodiments the predictive model stores a score indicative of a strength of benefit of a clinical trial for a given patient. In certain embodiments, the predictive model stores more comprehensive data about the outcomes, such as whether a condition of a patient improved, worsened, or remained unchanged, a length of time before an outcome was observed, and/or a set of side effects experienced by a patient. These data points may be aggregated within the model (e.g., as a score) or otherwise stored in the model with indicators of whether each data point is positive or negative.

At step 450, a predicted outcome is generated for the first patient based on the respective outcomes for each patient in the cohort. For example, the predictive model may output the predicted outcome in the form of a score that is determined based on the respective outcomes (e.g., by averaging or otherwise aggregating the respective outcomes from the cohort). For example, a similarity measure may be determined between the first patient and each respective patient in the cohort (e.g., based on attributes of the first patient and of each respective patient in the cohort), and the similarity measures may be used to aggregate the respective outcomes (e.g., the respective outcomes may be weighted based on the similarity measures).

At step 460, it is determined to refrain from recommending the potential clinical trial for the first patient based on the predicted outcome. For example, trial recommendation engine 144 of FIG. 1 may refrain from recommending the potential clinical trial due to the predicted outcome being negative, such as in the form of a score that is below a threshold. Trial recommendation engine 144 of FIG. 1 may recommend other clinical trials with positive predicted outcomes rather than the potential clinical trial.

Figure 5:
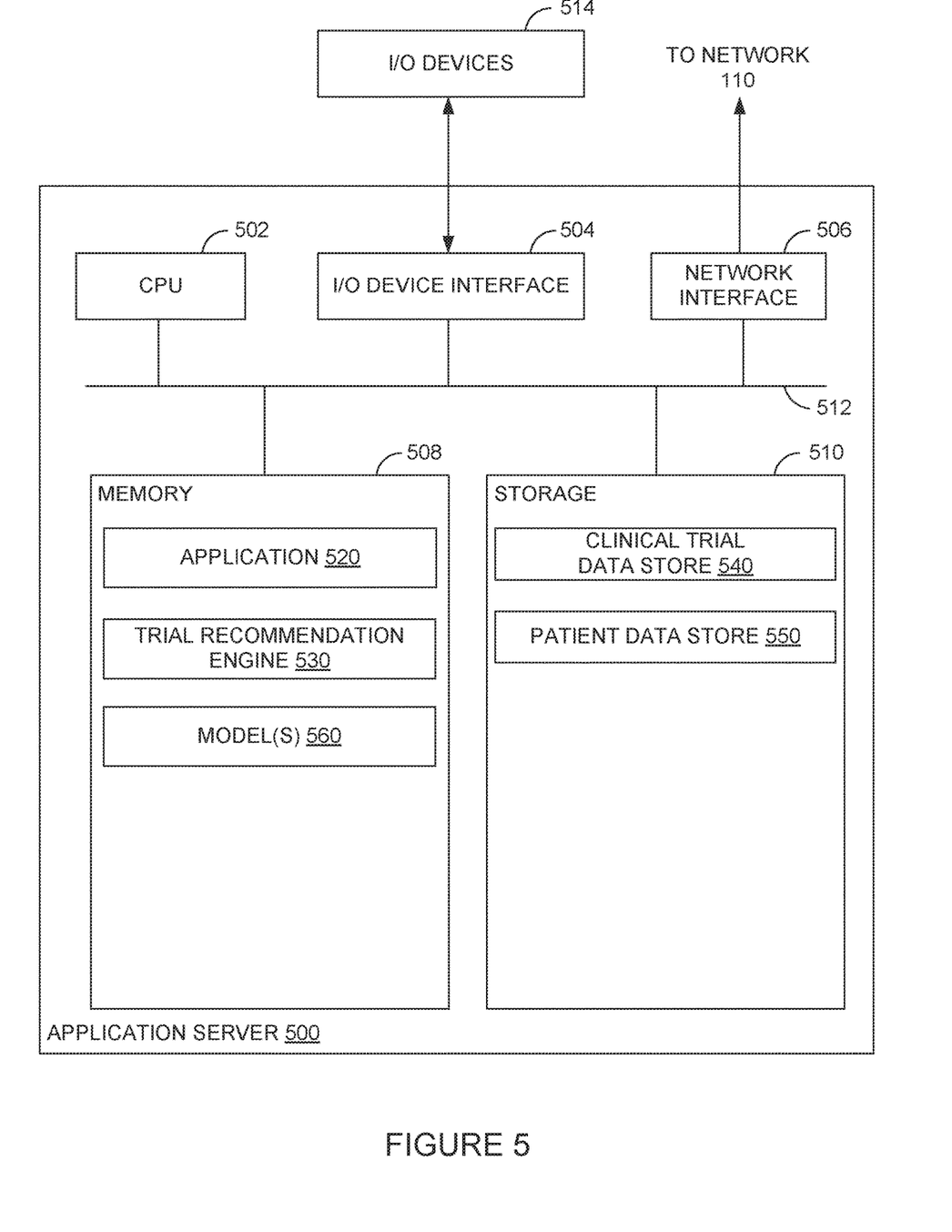
FIG. 5 illustrates an example system in which aspects of the present disclosure may be performed.

FIG. 5 depicts a computing system 500 with which embodiments of the present disclosure may be implemented. For example, computing system 500 may represent application server 140 of FIG. 1.

System 500 includes a central processing unit (CPU) 502, one or more I/O device interfaces 504 (that may provide connections for various I/O devices 514, such as keyboards, displays, mouse devices, and the like) to the system 500, network interface 506 (e.g., a physical network interface card), memory 508, storage 510, and an interconnect 512. It is noted that one or more components of system 500 may alternatively be located remotely and accessed via a network, such as network 110. It is further contemplated that one or more components of system 500 may comprise physical or virtualized components.

CPU 502 may receive and execute instructions stored in memory 508. Similarly, the CPU 502 may receive and store data related to applications in memory 508. The interconnect 512 transmits programming instructions and application data, among the CPU 502, I/O device interface 504, network interface 506, memory 508, and storage 510. CPU 502 is included to be representative of a single CPU, multiple CPUs, a single CPU having multiple processing cores, and other arrangements.

Additionally, the memory 508 may represent a random access memory. Storage 510 may be a disk drive, solid state drive, or a collection of storage devices distributed across multiple storage systems. Although shown as a single unit, the storage 510 may be a combination of fixed and/or removable storage devices, such as fixed disc drives, removable memory cards or optical storage, network attached storage (NAS), or a storage area-network (SAN).

Storage 510 comprises clinical trial data store 540 and patient data store 550, which are representative of clinical trial data store 150 and patient data store 160 of FIG. 1. As shown, memory 508 includes application 520, trial recommendation engine 530, and model(s) 560, which are representative of application 142 and trial recommendation engine 144 of FIG. 1 and model(s) 210 of FIG. 2.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Reference is made herein to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., application 142 and/or trial recommendation engine 144 of FIG. 1) or related data available in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A computer-implemented method comprising:
   receiving one or more attributes of a first patient;
   selecting a potential clinical trial for the first patient, based on the one or more attributes, using fuzzy logic that is based on degrees of association between the one or more attributes and particular attributes associated with the potential clinical trial;
   selecting, based on a clinician associated with the first patient, a machine learning model from a plurality of clinician-specific machine learning models, wherein each of the plurality of clinician-specific machine learning models has been generated by customizing an institutional baseline model based on preferences of a given clinician associated with an institution treating the first patient, wherein the institutional baseline model was trained based on institutional preferences of the institution treating the first patient;
   providing inputs to the machine learning model based on the one or more attributes of the first patient, wherein the machine learning model has been trained through a supervised learning process comprising:
      generating a training data set comprising features of patients associated with labels, wherein:
         each patient of the patients has undergone a respective clinical trial that is either (i) the potential clinical trial, or (ii) a clinically similar clinical trial to the potential clinical trial; and
         each label of the labels comprises an indicator of whether a given clinical trial was beneficial for a given patient of the patients based on feedback from the given patient and based on objective outcome data; and
      iteratively modifying the machine learning model based on the training data set;
   generating a predicted benefit of the potential clinical trial for the first patient, based on an output provided by the machine learning model in response to the inputs; and
   refraining from recommending the potential clinical trial for the first patient, based on the predicted benefit being below a threshold.

2. The computer-implemented method of claim 1, wherein selecting the potential clinical trial comprises:
   retrieving a plurality of clinical trials, wherein each of the plurality of clinical trials specifies a set of criteria; and
   identifying the potential clinical trial from the plurality of clinical trials based on determining that the one or more attributes satisfies the set of criteria specified for the potential clinical trial.

3. The computer-implemented method of claim 1, wherein clinically similar clinical trials are clinical trials that tested a same or a similar treatment option.

4. The computer-implemented method of claim 1, wherein the objective outcome data for each patient of the patients comprises at least one of:
   (i) an indication of whether a condition of the patient improved, worsened, or remained unchanged;
   (ii) an indication of a length of time before a respective outcome was observed; and
   (iii) an indication of a set of side effects experienced by the patient.

5. The computer-implemented method of claim 1, wherein the output from the machine learning model is based on a respective similarity between a respective patient of the patients and the first patient.

6. The computer-implemented method of claim 5, wherein the respective similarity is based on the one or more attributes of the first patient and one or more attributes of the respective patient of the patients.

7. The computer-implemented method of claim 1, the method further comprising recommending a second potential clinical trial for the first patient, based on a predicted benefit of the second potential clinical trial.

8. A system, comprising one or more processors and a computer-readable storage medium having computer-readable program code embodied therewith, the computer-readable program code executable by the one or more processors to perform a method, the method comprising:
receiving one or more attributes of a first patient;
selecting a potential clinical trial for the first patient, based on the one or more attributes, using fuzzy logic that is based on degrees of association between the one or more attributes and particular attributes associated with the potential clinical trial;
selecting, based on a clinician associated with the first patient, a machine learning model from a plurality of clinician-specific machine learning models, wherein each of the plurality of clinician-specific machine learning models has been generated by customizing an institutional baseline model based on preferences of a given clinician associated with an institution treating the first patient, wherein the institutional baseline model was trained based on institutional preferences of the institution treating the first patient;
providing inputs to the machine learning model based on the one or more attributes of the first patient, wherein the machine learning model has been trained through a supervised learning process comprising:
generating a training data set comprising features of patients associated with labels, wherein:
each patient of the patients has undergone a respective clinical trial that is either (i) the potential clinical trial, or (ii) a clinically similar clinical trial to the potential clinical trial; and
each label of the labels comprises an indicator of whether a given clinical trial was beneficial for a given patient of the patients based on feedback from the given patient and based on objective outcome data; and
iteratively modifying the machine learning model based on the training data set;
generating a predicted benefit of the potential clinical trial for the first patient, based on an output provided by the machine learning model in response to the inputs; and
refraining from recommending the potential clinical trial for the first patient, based on the predicted benefit being below a threshold.

9. The system of claim 8, wherein selecting the potential clinical trial comprises:
retrieving a plurality of clinical trials, wherein each of the plurality of clinical trials specifies a set of criteria; and
identifying the potential clinical trial from the plurality of clinical trials based on determining that the one or more attributes satisfies the set of criteria specified for the potential clinical trial.

10. The system of claim 8, wherein clinically similar clinical trials are clinical trials that tested a same or a similar treatment option.

11. The system of claim 8, wherein determining, wherein the objective outcome data for each patient of the patients comprises at least one of:
(i) an indication of whether a condition of the patient improved, worsened, or remained unchanged;
(ii) an indication of a length of time before a respective outcome was observed; and
(iii) an indication of a set of side effects experienced by the patient.

12. The system of claim 8, wherein the output from the machine learning model is based on a respective similarity between a respective patient of the patients and the first patient.

13. The system of claim 12, wherein the respective similarity is based on the one or more attributes of the first patient and one or more attributes of the respective patient of the patients.

14. The system of claim 8, the method further comprising recommending a second potential clinical trial for the first patient, based on a predicted benefit of the second potential clinical trial.

15. A computer-readable storage medium having computer-readable program code embodied therewith, the computer-readable program code executable by one or more computer processors to perform a method, the method comprising:
receiving one or more attributes of a first patient;
selecting a potential clinical trial for the first patient, based on the one or more attributes, using fuzzy logic that is based on degrees of association between the one or more attributes and particular attributes associated with the potential clinical trial;
selecting, based on a clinician associated with the first patient, a machine learning model from a plurality of clinician-specific machine learning models, wherein each of the plurality of clinician-specific machine learning models has been generated by customizing an institutional baseline model based on preferences of a given clinician associated with an institution treating the first patient, wherein the institutional baseline model was trained based on institutional preferences of the institution treating the first patient;
providing inputs to the machine learning model based on the one or more attributes of the first patient, wherein the machine learning model has been trained through a supervised learning process comprising:
generating a training data set comprising features of patients associated with labels, wherein:
each patient of the patients has undergone a respective clinical trial that is either (i) the potential clinical trial, or (ii) a clinically similar clinical trial to the potential clinical trial; and
each label of the labels comprises an indicator of whether a given clinical trial was beneficial for a given patient of the patients based on feedback from the given patient and based on objective outcome data; and
iteratively modifying the machine learning model based on the training data set;
generating a predicted benefit of the potential clinical trial for the first patient, based on an output provided by the machine learning model in response to the inputs; and
refraining from recommending the potential clinical trial for the first patient, based on the predicted benefit being below a threshold.

16. The computer-readable storage medium of claim 15, wherein selecting the potential clinical trial comprises:
retrieving a plurality of clinical trials, wherein each of the plurality of clinical trials specifies a set of criteria; and
identifying the potential clinical trial from the plurality of clinical trials based on determining that the one or more attributes satisfies the set of criteria specified for the potential clinical trial.

17. The computer-readable storage medium of claim 15, wherein clinically similar clinical trials are clinical trials that tested a same or a similar treatment option.

18. The computer-readable storage medium of claim 15, wherein the objective outcome data for each patient of the patients comprises at least one of:
   (i) an indication of whether a condition of the patient improved, worsened, or remained unchanged;
   (ii) an indication of a length of time before a respective outcome was observed; and
   (iii) an indication of a set of side effects experienced by the patient.

19. The computer-readable storage medium of claim 15, wherein the output from the machine learning model is based on a respective similarity between a respective patient of the patients and the first patient.

20. The computer-readable storage medium of claim 19, wherein the respective similarity is based on the one or more attributes of the first patient and one or more attributes of the respective patient of the patients.

* * * * *